United States Patent
Halpern

(10) Patent No.: US 6,179,871 B1
(45) Date of Patent: Jan. 30, 2001

(54) MEANS FOR CARTILAGE REPAIR

(76) Inventor: Alan A. Halpern, 1400 Low Rd., Kalamazoo, MI (US) 49008

(*) Notice: Under 35 U.S.C. 154(b), the term of this patent shall be extended for 0 days.

(21) Appl. No.: 08/749,095

(22) Filed: Nov. 14, 1996

Related U.S. Application Data

(62) Division of application No. 08/485,363, filed on Jun. 7, 1995, now Pat. No. 5,655,546.

(51) Int. Cl.$^7$ ....................................... A61F 2/02
(52) U.S. Cl. ..................... 623/11.11; 128/898; 424/484
(58) Field of Search ................... 623/18, 11, 16, 623/66; 128/898; 604/890.1, 891.1; 424/423, 484; 428/98, 357, 315.5–315.9

(56) References Cited

U.S. PATENT DOCUMENTS

| | | | |
|---|---|---|---|
| 5,062,991 | * | 11/1991 | Siiman et al. ................... 516/101 |
| 5,240,640 | * | 8/1993 | Siiman et al. ................... 516/95 X |

* cited by examiner

Primary Examiner—Gene Mancene
Assistant Examiner—Kelly O'Hara
(74) Attorney, Agent, or Firm—The Firm of Hueschen and Sage

(57) ABSTRACT

A method for repairing a defect in cartilage, comprising the provision of apertures in the cartilage by drilling holes at the base of the cartilage defect, which holes may enter the mesenchymal depot, introducing a porous scaffold material containing a plurality of magnetic particles into the apertures, and subsequently and sequentially injecting magnetically-tagged cartilage growth promoting materials such as various growth factors or chondrocytes into the area of the defect. The magnetically tagged growth promoting material is then drawn into the apertures by magnetic attraction of the magnetic particles contained in the porous scaffold material, either by virtue of the particles being permanently magnetic, or by the imposition of an external magnetic field. The present application claims the biodegradable porous scaffold material containing the plurality of magnetic particles.

6 Claims, 3 Drawing Sheets

MEANS FOR CARTILAGE REPAIR

The present application is a division of my prior-filed copending application Ser. No. 08/485,363, filed Jun. 7, 1995, now U.S. Pat. No. 5,655,546 issued Aug. 14, 1997.

BACKGROUND OF THE INVENTION

The present invention relates to the repair of joints of the human body, and is more particularly concerned with a method for repairing damaged cartilage and with means, especially the particular biodegradable scaffolding, utilized in carrying out the method.

PRIOR ART

The inability of adult articular cartilage for repair has been well recognized and has stimulated major interest in orthopaedic research. Even though considerable progress has been made in the field of articular reconstructive surgery, successful management of large chondral and osteochondral defects and degenerative lesions is still a challenge to the orthopaedic surgeon.

Current treatment is directed at replacement of articular surfaces with total joint reconstructions when sufficient destruction has occurred. A far more preferable approach would be to remedy or replace the articular cartilage defects before progressive and debilitating arthritis has occurred.

The number of individuals with symptomatic, identifiable, and potentially treatable cartilage defects is at least an order of magnitude greater than those who currently undergo some form of total joint arthroplasty.

For example, extrapolation of the published research findings for arthroscopic surgery of the knee in the United States would lead to an estimate of significant cartilage damage of the knee in over 250,000 patients. Numbers far greater than this are treated with nonsteroidal anti-inflammatory medication (NSAID) until their disease has progressed to the stage that a total joint arthroplasty is justifiable.

Multiple research centers in industry and academia are currently involved in pursuing a successful treatment for full thickness cartilage lesions. While some approaches are promising, there are currently no commercially viable treatment alternatives to date. The current approaches can be summarized into a few basic categories:
1. Abrasion arthroplasty
2. Chondroplasty
3. Drilling into the subchondral plate
4. Transplantation of autograft chondrocytes
5. Application of a variety of scaffolding materials including, collagen, polymers, polyglycolic acid, carbon fiber
6. Full thickness osteochondral allograft transplants
7. Continuous passive motion
8. Perichondrium transplants Previous studies have shown that chondrocytes from an allogenic source cultured in a composite collagen gel/fibrillar matrix could be used successfully to repair cartilage surface defects in a rabbit knee joint model (Grande et al; 1987). However, it would be clinically superior to be able to repair these defects by mobilizing the intrinsic repair response to push stem cells toward a chondrogenic lineage by the use of growth factors known to be mitogenic to such cells. Recent studies have shown that both periosteum and bone marrow have cellular populations that can be isolated in tissue culture and can form cartilage both in vivo and in vitro (Nakahara et al; 1990). Miura et al. (1992) have shown that exposure of periosteal tissue to transforming growth factor beta ($TGF_b$) in culture enhances chondrogenesis. Additional studies have shown the potent effect of fibroblast growth factor on connective tissue. The temporal sequence and bioavailability of growth factors in a wound repair model of articular cartilage are poorly understood.

In the publication, *TREATMENT OF DEEP CARTILAGE DEFECTS IN THE KNEE WITH AUTOLOGOUS CHONDROCYTE TRANSPLANTATION*, Brittberg et al. disclose the performance of autologous chondrocyte transplantation in 23 people with deep cartilage defects in the knee. Healthy chondrocytes obtained from an uninvolved area of the injured knee during arthroscopy were isolated and cultured in the laboratory for 14 to 21 days. The cultured chondrocytes were then injected into the area of the defect. The defect was covered with a sutured periosteal flap taken from the proximal medial tibia. Patients were followed for 16 to 66 months. Two years after transplantation 14 of the 16 patients studied with temporal condylar transplants had good to excellent results, with two of the patients requiring a second operation because of severe central wear in the transplants.

The idea that a magnetic field may have application to chondrogenesis or repair of a cartilage defect or treatment of arthritis is not new. However, to date, despite considerable research, no current approach is actually being used clinically for treatment of cartilage defects. The applications of magnetically related patents may be grouped into the following categories:

(1) The use of opposing magnets to act as an artificial joint.

(2) Application of a fluctuating magnetic field to induce chondrogenesis.

(3) Application of a magnetic field to influence the release of an active agent from a scaffolding.

(4) Creation of magnetic microspheres for intravascular delivery of a tagged agent, most commonly a chemotherapeutic agent for treatment of cancer.

(5) Contrast agents for NMR (nuclear magnetic resonance) imaging enhancement.

Magnetic means have previously been utilized in the laboratory technique of the prior art.

Senyei and Widder U.S. Pat. No. 4,230,685 (1980) describe a method for magnetic separation of cells utilizing magnetic microspheres. Claim is made for the preferential selection of a group of cells. A polymer mix is described.

Gordon U.S. Pat. No. 4,731,239 (1988) proposed a method for enhancing NMR imaging by use of ferromagnetic, paramagnetic, or diamagnetic particles composed of a number of constituents. This approach built on his previous patents U.S. Pat. No. 4,303,636 and U.S. Pat. No. 4,136,683 and U.S. Pat. No. 4,106,488. This series of patents deals with NMR image improvement and particles which are administered intravenously, the goal being to define metabolic diseases or malignant states. Gordon has an additional patent, 1988 U.S. Pat. No. 4,735,796 in which he proposes the use of ferromagnetic, diamagnetic or paramagnetic particles useful in the diagnosis and treatment of disease. In this use, he proposes to use the magnetic particles to enhance the destructive capability of an external field to treat inflammatory arthritis.

Similarly, Widder U.S. Pat. No. 4,675,173 (1987) proposed a method of magnetic resonance imaging of the liver and spleen using ferromagnetic microspheres given intravenously. Widder had a subsequent patent, 1989 U.S. Pat. No. 4,849,210 entitled "Magnetic resonance imaging of liver and spleen with superparamagnetic contract agents".

Prior Art with Arthroscopically Applied Techniques

Shah U.S. Pat. No. 5,263,987 (1993) proposed applying a series of small plugs to the damaged cartilage surface, replacing a joint utilizing a plurality of joint surface members which are attached to a prepared surface arthroscopically. This approach seeks to create an artificial joint by a series of tack-like structures composed of artificial materials similar to an artificial knee replacement. This is not similar to my approach, but because the implants are inserted arthroscopically, it is mentioned.

Prior Art with Magnetically-tagged Microspheres

Yen et al. U.S. Pat. No. 4,157,323 (1979) proposed using metal containing polymeric functional microspheres for laboratory separation of labelled cells, but also concentration within the body for treatment of a malignant tumor by applying a magnetic field to the location.

Morris U.S. Pat. No. 4,331,654 (1982) proposed the use of magnetically localizable biodegradable lipid microspheres for delivery of drugs.

Molday U.S. Pat. No. 4,452,773 (1984) described colloidal sized particles composed of magnetic iron oxide which could be covalently bonded to antibodies, enzymes and other biological molecules for use in labelling and separating cells, cellular membranes and other biological particles. He describes a specific particle which I do not use and applies this to a different use.

Widder U.S. Pat. No. 4,345,588 (1982) described a method of delivering a therapeutic agent to a target capillary bed. In his case, the agent was administered intravascularly and given for the purpose of delivering an oncolytic agent to a malignant site. Specifically, his approach requires a capillary bed. Furthermore, his approach concerns cancer chemotherapy.

In Widder U.S. Pat. No. 4,247,406 (1981) the agent is described as intravascularly administered but more specifically described as a biodegradable carrier comprised of micro-spheres formed from an amino acid polymer matrix with magnetic particles embedded therein. This agent is described as being delivered solely intravascularly and with the purpose of concentrating a chemotherapeutic agent.

Prior Art with Matrix and Biodegradable Approaches and Mesenchymal Cells

In Caplan et al. U.S. Pat. No. 4,609,551 (1984) a soluble bone protein is purified and combined with fibroblast cells to form a protein-cell combination and further combined with a biodegradable carrier to form a mass.

In Caplan et al. U.S. Pat. No. 5,197,985 (1990) a method is described for inducing marrow-derived mesenchymal stem cells to differentiate into cartilage forming cells. The method requires that the cells be isolated, purified, and cultured in a medium (culturally expanded). The cells are then applied to a porous carrier comprised of about 60% hydroxyapatite and 40% tricalciumphosphate.

A subsequent patent, Caplan et al. U.S. Pat. No. 5,226,914 (1993) Method for treating connective tissue disorders", addresses the use of culturally expanded purified human marrow-derived mesenchymal cells. This patent requires the external culturing and isolation of cells. He proposes the formatting of the cells in carriers constructed of collagen or fibrin. The carriers are described as pliable to mold to the shape of the defect.

Hunziker U.S. Pat. No. 5,206,023 (1993) describes a method to induce cartilage formation in which the defect is filled or otherwise dressed with a biodegradable matrix which contains a proliferative agent for stimulating chondrogenesis. Specifically, he refers to filling the defect with the matrix containing an agent such as TGF-Beta encapsulated in liposomes, and then covering the surface with fibrin glue.

Nevo et al. U.S. Pat. No. 4,642,120 (1987) proposed an approach to the repair of cartilage and bone by use of gel composed of committed embryonal chondrocytes of any kind of mesenchyme originated cells. The cells are combined with a biological glue such as fibrinogen, thrombin and a protease inhibitor and the defect is filled with the sample which is described as being pressed into the injured site.

Vacanti et al. have published extensively and have a patent on the application of a biodegradable matrix. They place significant emphasis on their ability to shape the matrix to the shape of the defect. They are also interested in applications to bone defects, as applies to orthopedics and to plastic surgery.

A patent to Vacanti et al. U.S. Pat. No. 5,041,138 (1991) "Neomorphogenesis Of Cartilage In Vivo From Cell Culture", makes claims for a biocompatible, biodegradable synthetic matrix to replace defective or missing cartilage.

Folkman et al. U.S. Pat. No. 5,019,372 (1991) proposed a magnetically modulated polymeric drug release system. This approach proposed that a fluctuating magnetic field could be applied to a responsive substance implanted in the body to cause release of a biologically active substance.

Prior Art with an Electromagnetic Field Per Se

Liboff et al. U.S. Pat. No. 5,067,940 (1991) proposed a method and apparatus for controlling the growth of cartilage by application of a controlled, fluctuating directionally oriented magnetic field parallel to a predetermined axis, utilizing a preselected ratio of frequency to average flux density. To date, the data supporting this approach has not proven convincing.

Baylink U.S. Pat. No. 5,330,410 (1994) proposed a method for increased production of growth factor in living tissue using an applied fluctuating magnetic field.

Gordon U.S. Pat. No. 4,758,429 (1988) proposed a method for the treatment of arthritis and inflammatory joint diseases. His approach was to activate magnetic particles to allow destruction of the reactive cell and diminuation of the destructive process in the joint. Again, he is using the magnetic effect solely for destruction of the offending cells.

OBJECTS OF THE INVENTION

It is an object of the present invention to utilize magnetically directed growth factors, biodegradable ferromagnetic, paramagnetic, or diamagnetic polymers, and chondrocytes to successfully repair cartilage defects in a joint having cartilage defects.

It is a further object to repair cartilage defects by placing a biodegradable polymer with magnetic particles or mesenchymal cells impregnated into the polymer at the base of a cartilage defect.

It is a further object to attract growth factors tagged with magnetic particles or chondrocytes tagged with magnetic particles to a cartilage defect by the use of a permanent magnetic effect from the particles or as a result of an externally applied magnetic field.

It is an additional object to utilize growth factors sequentially or in cascade injected into a joint having a cartilage defect to accomplish cartilage repair or formation.

It is a primary object to provide a method for treating a patient having a cartilage defect to accomplish cartilage repair or formation by implanting a biodegradable polymer with magnetic particles, and to be able to treat the patient subsequently by sequential application of various growth factors, chondrocytes, or other growth stimulating materials to the site of the defect without the need for further major surgery.

SUMMARY OF THE INVENTION

According to the invention, a clinically viable therapy for osteochondral defects include the implantation of ferromagnetic dipoles in such defects and subsequent staged intra-articular injections of magnetically tagged growth factors. The growth factors migrate into the defect and promote chondrogenesis and subsequent repair. Successful chondrogenesis is thus achieved in a cascade fashion similar to osteogenesis and clotting.

Clinical application of these principles is achieved by localization of the chondrogenic effect utilizing magnetically directed chondrogenesis. The magnetically targeted particles are directed to the cartilage defect through the implantation of ferromagnetic material in the cartilage defect area, which may involve a supplementary external magnetic field. This, while more cumbersome, offers the advantage of improved modulation of the process and pulsatile control of the implantation.

What we believe to be our invention, then, inter alia, comprises the following, singly or in, is thus further define in the claims hereof.

DESCRIPTION OF THE PREFERRED EMBODIMENTS

Figure 1:
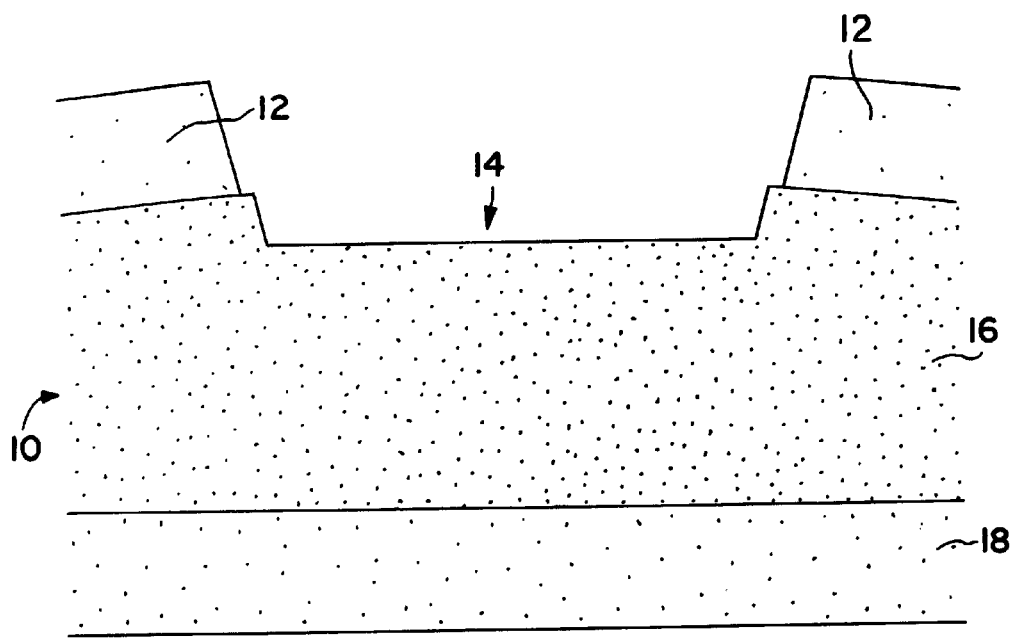
FIG. 1 is a fragmentary cross-sectional view of the end portion of a bone articulated in a joint, the bone having an articular cartilage defect.

Experimental Design and Methods
General Methods

Isolation of periosteal culture: Periosteal tissue is isolated from the distal femora and proximal tibia of NZW rabbits. In a sterile laminar flow hood, the periostea are placed into a 100 mm. petri dish and with a No. 15 scalpel and forceps are diced into small (1 mm$^2$) pieces. The pieces are then transferred into a 60 mm petri dish as explants and prepared for three dimensional culture.

Isolation of marrow mesenchymal stem cells: After periostea have been isolated from the bone surface, the diaphysis of the femora are resected and the marrow cavity is flushed from one end with an injection of Tyrodes balanced salt solution. The resulting marrow plug is then prepared into a single cell suspension by successively drawing the tissue through increasingly narrower syringe gores, starting with an 18 gauge syringe and ultimately ending with a 22 gauge. The final cell suspension is then passed through a 20 μm nylon filter. Cells are then counted, tested for viability, and then prepared for suspension culture.

Chondrocyte Isolation: Articular cartilage samples obtained from donor rabbits are treated as follows to isolate free chondrocytes. The articular cartilage specimens are transferred to a sterile 60 mm petri dish and diced into pieces of approximately 1 mm$^3$ and then transferred to a glass spinner flask. To this flask 15 ml of RPM-1640 medium with 25 Mm HEPES buffer (MA Bioproducts) containing clostridial collagenase (Sigma, type 1A 0.37 mg/ml), deoxyribo-nuclease (DNASE) (Worthington, Activity:133 U/mg, 15 mg/ml), testicular hyaluronidase (Sigma, type IS;10 mg/m 1), and penicillin-streptomycin (5,000 u/5000 u; 1% v/v) is added. This enzyme-medium mixture is filter-sterilized (0.45 micrometers, nylon membrane) and the samples are spun on a magnetic stirrer at 370 C for 4–6 hours. To harvest the cells, extracellular matrix debris is removed by passing the entire medium-cell mixture through a sterile 120 μm nylon mesh (Nitex Corp.). This is followed by centrifuging at 1500 rmp for 5 minutes. The cell pellet is resuspended with phosphate buffered saline and centrifuged. The washing procedure is repeated twice. The cells are counted and viability tested by the Trypan-blue exclusion method. Chondrocytes are then spun into a pellet for later suspension in agarose.

Tissue culture conditions: To prepare a three dimensional culture system, a 1% solution (W/v) of a low melting point agarose is prepared in phosphate buffered saline (PBS), and autoclaved. Upon cooling, chondrocytes or marrow cells are mixed into the still liquid solution, stirred well and then overlaid into 60 mm petri dishes. This results in an even spatial distribution of cells in a three dimensional matrix. For periosteal cultures, cooled agarose is overlaid into 60 mm petri dishes and explants of periosteal tissue are placed into the soft agarose. After six hours to allow adequate gelation, cultures are overlaid with a layer of medium. Primary cultures of periosteal cells and chondrocytes are cultured in Medium "A" as described by Osborn et al. This is a low serum formulation (50/50 DMEM/Hams F-12) which will minimize extraneous effects of calf serum. Cultures are fed fresh medium every other day, and examined daily for growth using an inverted phase contrast microscope.

EXAMPLE 1

Three dimensional cultures are prepared from both tissue types as previously described. After 48 hours to allow equilibration of cultures, medium is replaced with medium containing the following supplements: basic fibroblast growth factor (bFGF) at 0.1, 1.0, and 10 ng/ml; transforming growth factor beta (TGFb) 3 ng/ml. Control samples are fed med. A alone. Replicate culture samples are harvested at days 3, 7, and 14 and treated as described below.
Proteoglycan Synthesis:

Cultures are incubated with sulfate$^{35}$ for 4 hours (10 uCi/ml). At the end of incubation, labeled medium is aspirated off and the samples are rinsed five times with phosphate buffered saline. Samples are then extracted with 4M GuHCl, pH 5.6 at 4° C. for 24 hours. The extracted sample is then run on a Sephadex G-25 column and the high molecular weight fractions are pooled and scintillation counted.
Collagen Synthesis:

Cultures are incubated with tritiated proline for 4 hours, washed extensively and extracted with TCA. Samples are then scintillation counted.

Thymidine Incorporation:

Cultures are incubated with tritiated thymidine for 24 hours prior to sample harvest, extracted with TCA and scintillation counted.

All data is expressed in CPM and normalized by DNA content using the fluorometric dye binding assay with Hoechst 33258.

EXAMPLE 2

This example is designed to critically evaluate the ability of ferromagnetic dipoles to increase the rate of protein synthesis and proliferation in this culture system.

Primary cultures of periosteum tissue, marrow cells and chondrocytes are prepared and cultured as previously described. Experimental groups are prepared with ferromagnetic dipoles placed in a matrix grid pattern every 2 mm glued to the bottom of the dishes so as to be oriented perpendicular to the dish bottom. The agarose/cell suspension is then overlaid on top of the dipole array. The study is conducted in an analogous fashion to Example 1 with the following differences: Growth factor containing mediums are specially tagged to magnetic beads. Control sample are treated in a similar fashion but lack the ferromagnetic dipole array in the bottom of the petri dish.

EXAMPLE 3

This example is conducted in an identical fashion as Example 1 with the exception that medium supplemented with FGF alone (-TGFb) added for the first 5 days in culture. Cultures are then fed the medium containing the TGFb (3 ng/ml) and FGF is no longer used. The medium containing the TGFb is continued for a total culture time of two weeks and samples are treated as described in Example 1. The dosage of FGF used is determined from the optimal response found from the results of Example 1. Control cultures are fed med. A alone.

EXAMPLE 4

This example tests the reverse temporal sequence for growth factor addition as stated in Example 2. In this experiment TGFb (3 ng/ml) alone is added initially followed on a 5 day FGF. Again, samples are treated as described above with respect to dosages and controls.

EXAMPLE 5

This example critically evaluates the ability of ferromagnetic dipoles to increase the rates of protein synthesis and proliferation in this culture system.

Primary cultures of periosteum tissue, marrow cells and chondrocytes are prepared and cultured as previously described. Experimental groups are prepared with ferromagnetic dipoles placed in a metric grid pattern every 2 mm glued to the bottom of the dishes so as to e oriented perpendicular to the dish bottom. The agarose/cell suspension is then overlaid on top of the dipole array. The study is conducted in a fashion analogous to Example 1 with the following differences: growth factor containing mediums are specially tagged to magnetic beads. Control samples are treated in a similar fashion but lack the ferromagnetic dipole array in the bottom of the petri dish.

EXAMPLE 6

Clinically, a surgical procedure for the sequential application of growth factor chondrogenesis utilizing magnetically targeted particles is carried out as follows.

Referring to FIG. 1, a portion of a joint 10 is diagrammatically shown, comprising a cartilage layer 12, having a cartilage defect 14. Below the cartilage layer 12 is a subchondral bone layer 16, and a mesenchymal cell depot 18.

Figure 2:
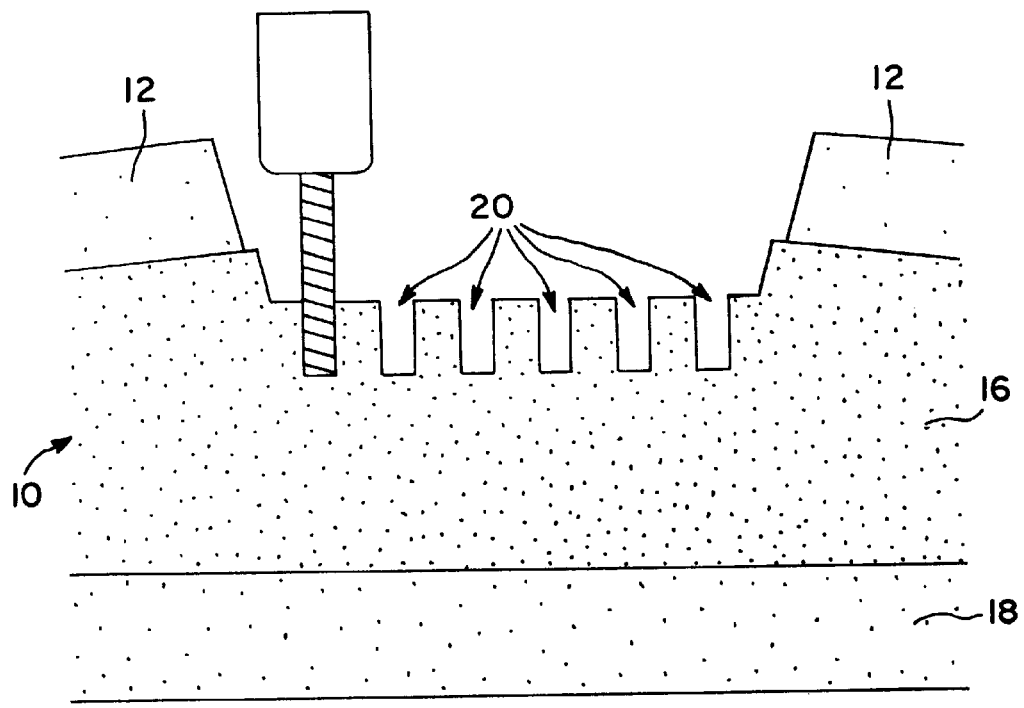
FIG. 2 is a fragmentary cross-sectional view of the end portion of a bone articulated in a joint, the bone having an articular cartilage defect, as shown in FIG. 1, and illustrating the method of drilling apertures or holes into the bone.

Referring to FIG. 2, a series of holes 20 are drilled at the site of the cartilage defect extending into the subchondral bone, and femorally into the mesenchymal cell depot.

Figure 3:
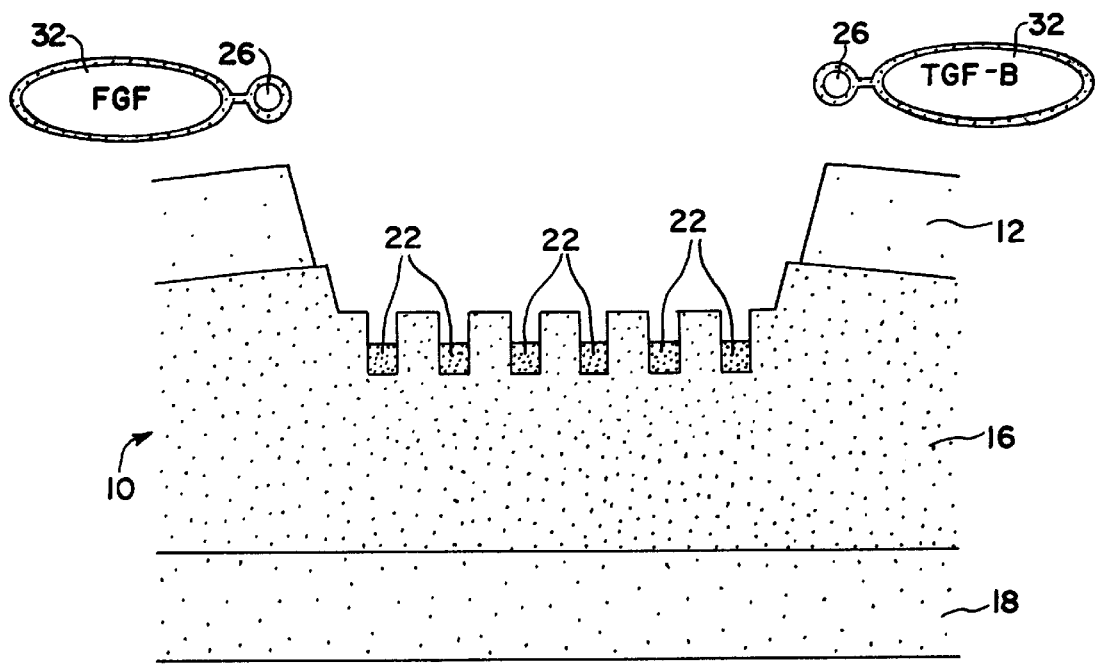
FIG. 3 is a view similar to that of FIG. 2, but showing the apertures filled with a material having magnetic particles dispersed therein.

Referring to FIG. 3, an amalgam containing a metabolically-porous scaffolding material, such as collagen or synthetic alternatives, is added to a magnetically active pellet. This cylindrical mass 22 is then injected into the drill holes.

Figure 4:
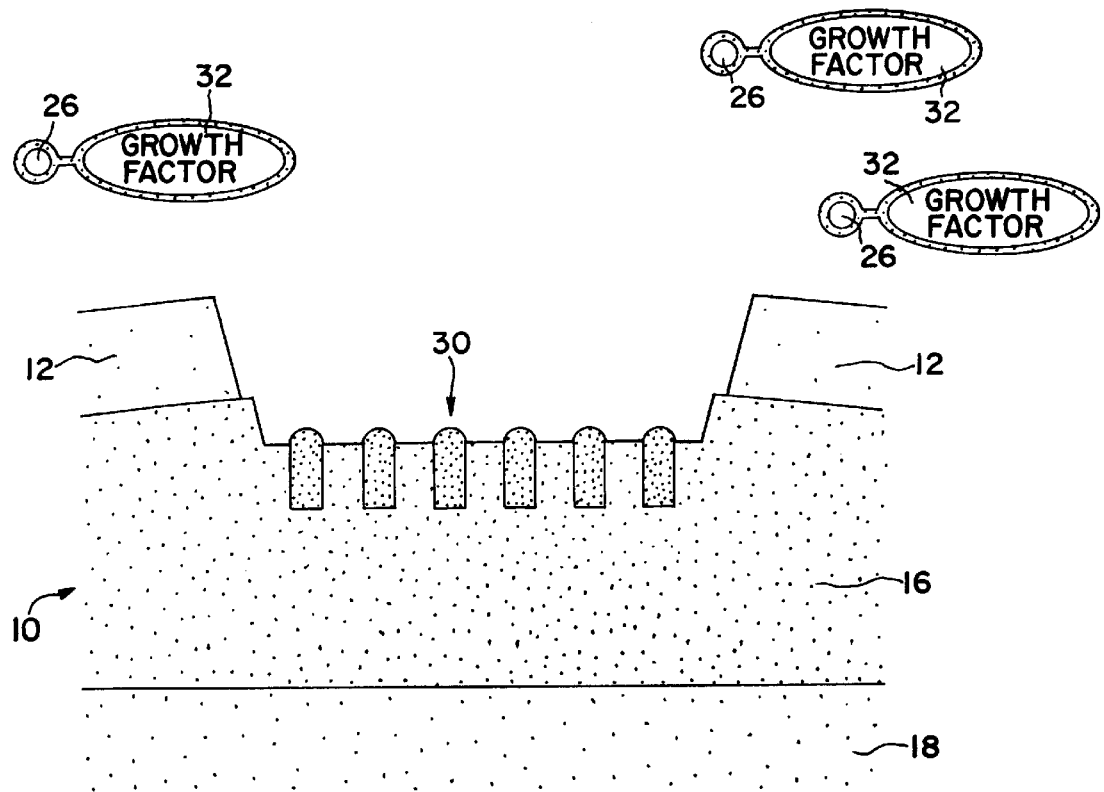
FIG. 4 is a view similar to that of FIG. 3, and having a porous scaffold filling the articular defect and the apertures above the material containing the magnetic particles, and FIG. 5. is a side elevational view, partially in cross-section, diagrammatically showing the application of an external magnetic force across the joint.

As shown in FIG. 4, the entire holes may be filled with the porous scaffolding material and magnetic material 22. A series of growth factors 32 attached to magnetic particles 26 are then injected into the joint in a timed sequence. Continuous passive motion or controlled range of motion exercises and limited weight bearing are applied to the surface, the scaffolding serving to protect the chondrogenesis. Sequential injections of various growth factors or chondrocytes which are magnetically tagged may be made at various time intervals.

Figure 5:
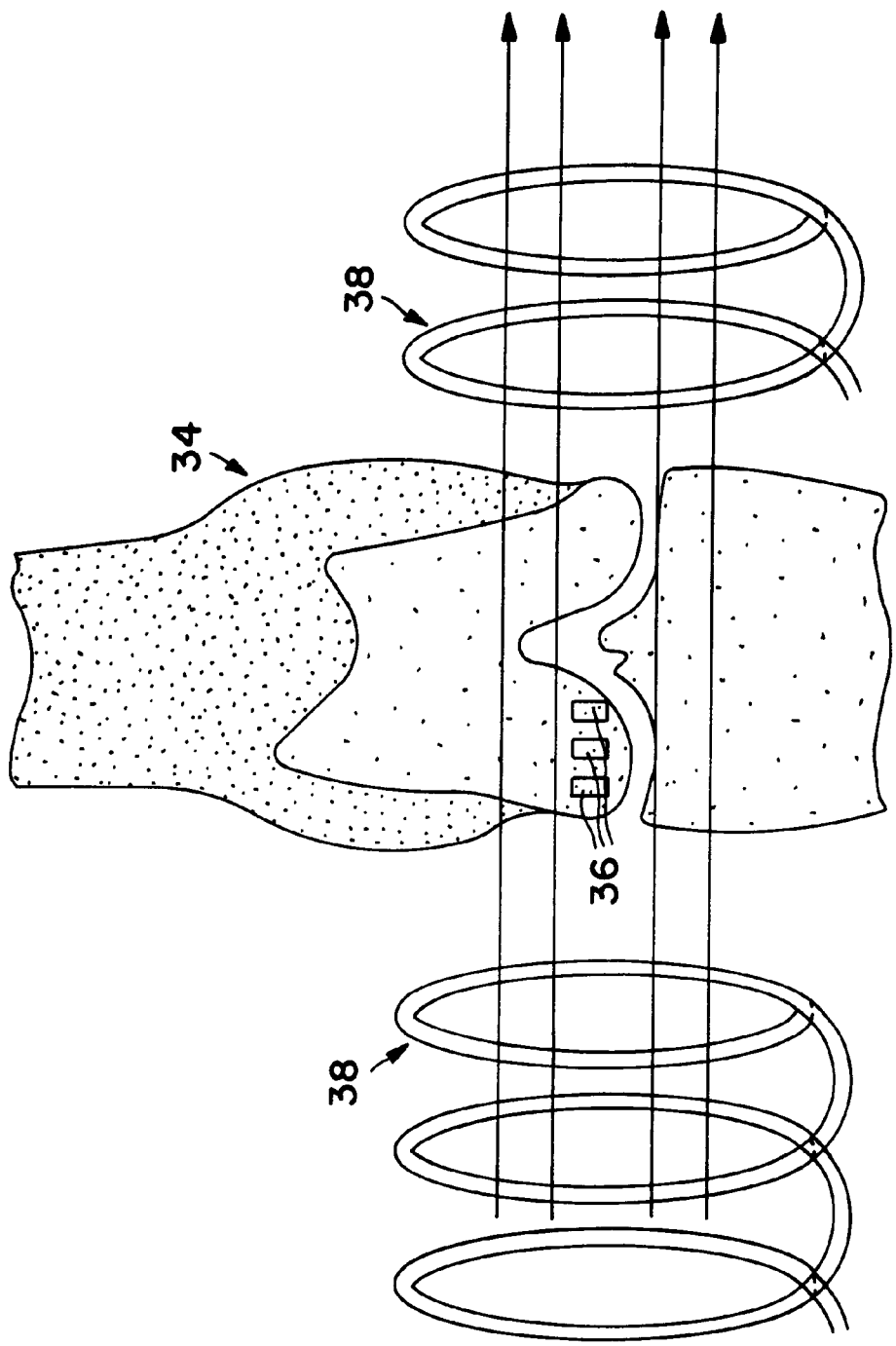

Referring to FIG. 5, a joint 34 is diagrammatically shown having cartilage defects which have been implanted with magnetic particle-containing scaffolding 36, to which an external magnetic field 38 is applied. The magnetic field 38 magnetizes the magnetic particles and causes them to attract the growth factors attached to the magnetically tagged particles which are subsequently injected into the joint in a timed sequence.

Alternatively, the external magnetic field may be utilized to direct the magnetically tagged growth factor to the proper geometric position in the desired sequence in place of the magnetically active pellet which is incorporated in the scaffolding material.

The magnetic particles implanted at the site of the cartilage defect may be energized by an external magnetic field with a differential effect on the selected growth factors. The implantation of the magnetically tagged implant can be accomplished arthroscopically, utilizing instrumentation specifically designed for this task.

Among the materials which stimulate repair of cartilage are cartilage derived growth factor (CDGF), a cationic polypeptide which stimulates the proliferation of cultured mouse fibroblasts, as well as chondrocytes and endothelial cells, transforming growth factor Beta (TGF-beta), a multifunctional peptide, which regulates the proliferation and differentiation of many cell types. Other growth factors are connective tissue activating peptides (CTAP), insulin-like growth factor (IGF-1), acidic fibroblast growth factor (aFGF), and basic fibroblast growth factor (bFGF).

According to the invention, it has been demonstrated in the laboratory that growth factors can be tagged with a magnetically active particle, and maintain their activity. This is the first time that chondrogenic and osteogenic growth factors have been so tagged and the factors demonstrated to be active. Specifically, a Partisome particle has been attached to bFGF and to TGF-Beta, and it has been experimentally proved that the growth factor remains biochemically active.

A polymer has been constructed in the laboratory impregnated with ferromagnetic iron particles. These impregnated polymers are implanted in rabbits in an initial experiment to establish biocompatibility and effectiveness.

It has been further demonstrated that one can attach the Partisome particle to a chondrocyte itself. The chondrocyte remains viable, and maintains viability indefinitely. Furthermore, it has been shown that the chondrocyte can be localized to a desired area by use of an external magnet, ferromagnetic particles embedded in a biodegradable polymer, and an external magnetic field. Again, this represents the first time that a chondrocyte has been magnetically tagged and directed to a desired location with the chondrocyte remaining viable.

The magnetic particles which are being employed herein are supplied by Bioquest, Inc. (formerly Molecular Bio-Quest, Inc.) of Atkinson, N.H. The material is disclosed in a patent to Chagnon et al, 1993 (U.S. Pat. No. 5,225,282) entitled "Biodegradable Magnetic Microcluster Comprising Non-Magnetic Metal or Metal Oxide Particles Coated With a Functionalized Polymer," and forms the basis of the ability to tag the growth factors and the chondrocytes. This work builds on a previous patent of same assignee Chagnon et al, 1991 (U.S. Pat. No. 5,071,076) "Method For Producing Magnetic Microparticles From Metallocenes", Chagnon, 1992 (U.S. Pat. No. 5,147,573) "Super-paramagnetic Liquid and Colloids". Also related is a patent of Daniel Grande entitled "Technique For Healing Lesions In Cartilage", 1989 (U.S. Pat. No. 4,846,835). He proposed at that time that the chondrocytes would be seeded in a three dimensional collagen matrix which served as the graft material. The graft would be held in place by a periosteal flap. The disclosures of these patents are hereby incorporated by reference. The Swedish researchers referred to above built on this approach, but did not use any scaffolding. It now appears to be the case that the scaffolding, which is present in the actual cartilage defect, interferes with needed chondrogenesis and may not be needed or appropriate. The present scaffolding sits in a series of cylinders below the defect and seeks to attract the growth factors or chondrocytes to the site.

It is to be understood that the present invention is not to be limited to the exact details of operation, or to the exact compounds, compositions, methods, procedures, or embodiments shown and described, as various modifications and equivalents will be apparent to one skilled in the art, wherefore the present invention is to be limited only by the full scope which can be legally accorded to the appended claims.

I claim:

1. A solid magnetic substrate, said substrate consisting of a porous biodegradable scaffold material containing a plurality of magnetic particles having a size of 0.05 to 500 microns, said substrate being adapted for insertion into an aperture provided in the subchondral base of a cartilage which has a defect in need of repair, and beneath the said defect, for attracting magnetically-tagged cartilage growth-promoting material to the defect, said biodegradable scaffold material having a pore size of 50 to 400 microns to admit entry thereinto of mesenchymal or stem cells.

2. A substrate of claim 1, wherein the magnetic particles contained in said scaffold material are permanently magnetized.

3. A substrate of claim 1, wherein said scaffold material is selected from the group consisting of collagen, biodegradable polymers, polyglycolic acid and carbon fibers.

4. A substrate of claim 1, wherein said porous scaffold material is collagen.

5. A substrate of claim 1, wherein said porous scaffold material is a biodegradable polymer.

6. A substrate of claim 5, wherein said polymer comprises a mixture of polylactic acid and polyglycolic acid combined with magnetic particles.

* * * * *

UNITED STATES PATENT AND TRADEMARK OFFICE
CERTIFICATE OF CORRECTION

| | |
|---|---|
| PATENT NO. | : 6,179,871 B1 |
| DATED | : January 30, 2001 |
| INVENTOR(S) | : Alan A. Halpern |

Page 1 of 1

It is certified that error appears in the above-identified patent and that said Letters Patent is hereby corrected as shown below:

Column 3,
Line 53, change "Method" to -- "Method --.

Column 5,
Line 28 (approx), "define" at the end of the line should read -- defined --.

Signed and Sealed this

Twenty-third Day of October, 2001

Attest:

Attesting Officer

NICHOLAS P. GODICI
Acting Director of the United States Patent and Trademark Office